(12) United States Patent
Standley et al.

(10) Patent No.: US 11,116,903 B2
(45) Date of Patent: Sep. 14, 2021

(54) COMPRESSION SEAL FOR USE WITH A LIQUID COMPONENT STORAGE VIAL OF AN AUTO-INJECTOR

(71) Applicant: Windgap Medical, Inc., Somerville, MA (US)

(72) Inventors: Adam Standley, Boston, MA (US); Cole Constantineau, Cambridge, MA (US); Christopher Stepanian, Somerville, MA (US); Brent Buchine, Austin, TX (US); Jeffrey Thomas Chagnon, Somerville, MA (US)

(73) Assignee: Windgap Medical, Inc, Watertown, MA (US)

( * ) Notice: Subject to any disclaimer, the term of this patent is extended or adjusted under 35 U.S.C. 154(b) by 613 days.

(21) Appl. No.: 15/891,459

(22) Filed: Feb. 8, 2018

(65) Prior Publication Data
US 2018/0161501 A1    Jun. 14, 2018

Related U.S. Application Data

(63) Continuation-in-part of application No. 15/034,967, filed on Aug. 1, 2016, now Pat. No. 9,907,911, which
(Continued)

(51) Int. Cl.
*A61M 5/19* (2006.01)
*A61M 5/20* (2006.01)
(Continued)

(52) U.S. Cl.
CPC ............ *A61M 5/19* (2013.01); *A61M 5/2033* (2013.01); *A61M 5/2066* (2013.01);
(Continued)

(58) Field of Classification Search
CPC ...... A61M 5/2448; A61M 5/284; A61M 5/19; A61M 5/2066; A61M 5/31596;
(Continued)

(56) References Cited

U.S. PATENT DOCUMENTS

| 3,680,558 A | 8/1972 | Kapelowitz |
| 3,946,732 A | 3/1976 | Hurscham |

(Continued)

FOREIGN PATENT DOCUMENTS

| EP | 0961612 A1 | 12/1999 |
| FR | 2741810 B1 | 2/1998 |

(Continued)

*Primary Examiner* — Amber R Stiles
*Assistant Examiner* — Alexandra Lalonde
(74) *Attorney, Agent, or Firm* — Ascentage Patent Law, LLC; Travis Lee Johnson

(57) ABSTRACT

Contemplated herein is a medication mixing device which can include a housing having therein a first chamber containing a first medicament component and a second chamber provided containing a second medicament component provided with a sealing structure selectively isolating the first chamber from the second chamber. The sealing structure can include a first sealing component having a first sealing interface and a second sealing component having a second sealing interface wherein a first compression force can be applied to the first and second sealing components causes the sealing interfaces to form a seal. The first compression force can then be configured to allow the first sealing component and the second sealing component to maintain at least one degree of freedom with respect to one another.

14 Claims, 10 Drawing Sheets

Related U.S. Application Data is a continuation-in-part of application No. PCT/US2015/045761, filed on Aug. 18, 2015.

(60) Provisional application No. 62/204,940, filed on Aug. 13, 2015, provisional application No. 62/126,011, filed on Feb. 27, 2015, provisional application No. 62/120,792, filed on Feb. 25, 2015, provisional application No. 62/061,664, filed on Oct. 8, 2014, provisional application No. 62/038,386, filed on Aug. 18, 2014, provisional application No. 62/456,727, filed on Feb. 9, 2017.

(51) Int. Cl.
*A61M 5/315* (2006.01)
*A61M 5/28* (2006.01)
*A61M 39/22* (2006.01)
*A61M 5/32* (2006.01)
*A61M 5/31* (2006.01)

(52) U.S. Cl.
CPC ........ *A61M 5/288* (2013.01); *A61M 5/31596* (2013.01); *A61M 5/3243* (2013.01); *A61M 39/22* (2013.01); *A61M 5/2053* (2013.01); *A61M 5/28* (2013.01); *A61M 5/3202* (2013.01); *A61M 5/3245* (2013.01); *A61M 5/3271* (2013.01); *A61M 2005/206* (2013.01); *A61M 2005/2013* (2013.01); *A61M 2005/3128* (2013.01)

(58) Field of Classification Search
CPC .. A61M 2005/1787; A61M 2005/3128; A61M 5/16827; A61M 5/2033; A61M 5/288; A61M 5/283; A61M 5/2053; A61M 5/3294; A61M 39/22; A61M 2005/2013; A61M 2005/2451; A61M 3/005
See application file for complete search history.

(56) References Cited

U.S. PATENT DOCUMENTS

| | | |
|---|---|---|
| 4,031,892 A | 6/1977 | Hurschman |
| 4,060,082 A | 11/1977 | Lindberg et al. |
| 4,529,403 A | 7/1985 | Kamstra |
| 4,643,721 A | 2/1987 | Brunet |
| 4,755,169 A | 7/1988 | Sarnoff et al. |
| 5,360,410 A | 11/1994 | Wacks |
| 5,569,193 A | 10/1996 | Hofstetter et al. |
| 5,704,918 A | 1/1998 | Higashikawa |
| 5,899,881 A | 5/1999 | Grimard et al. |
| 6,149,628 A | 11/2000 | Szapiro et al. |
| 6,309,372 B1 | 10/2001 | Fischer et al. |
| 6,641,561 B1 | 11/2003 | Hill et al. |
| 6,656,150 B2 | 12/2003 | Hill et al. |
| 6,770,052 B2 | 8/2004 | Hill et al. |
| 6,793,646 B1 | 9/2004 | Giambattista et al. |
| 6,852,103 B2 | 2/2005 | Fowles et al. |
| 6,953,445 B2 | 10/2005 | Wilmot et al. |
| 7,449,012 B2 | 11/2008 | Young et al. |
| 7,544,189 B2 | 6/2009 | Griffiths |
| 7,556,614 B2 | 7/2009 | Griffiths et al. |
| 7,608,055 B2 | 10/2009 | Griffiths et al. |
| 7,621,887 B2 | 11/2009 | Griffiths et al. |
| 7,678,073 B2 | 3/2010 | Griffiths et al. |
| 7,749,190 B2 | 7/2010 | Griffiths et al. |
| 7,757,370 B2 | 7/2010 | Griffiths |
| 7,776,015 B2 | 8/2010 | Sadowski et al. |
| 7,947,742 B2 | 5/2011 | Batycky et al. |
| 8,057,427 B2 | 11/2011 | Griffiths et al. |
| 8,092,420 B2 | 1/2012 | Bendek et al. |
| 8,123,719 B2 | 2/2012 | Edwards et al. |
| 8,177,758 B2 | 5/2012 | Brooks et al. |
| 8,187,220 B2 | 5/2012 | Griffiths et al. |
| 8,251,947 B2 | 8/2012 | Kramer et al. |
| 8,496,619 B2 | 7/2013 | Kramer et al. |
| 8,506,526 B2 | 8/2013 | Griffiths et al. |
| 8,568,367 B2 | 10/2013 | Griffiths et al. |
| 8,613,720 B2 | 12/2013 | Bendek et al. |
| 8,632,504 B2 | 1/2014 | Young |
| RE44,847 E | 4/2014 | Sadowski et al. |
| 8,696,618 B2 | 4/2014 | Kramer et al. |
| 8,784,372 B1 | 7/2014 | Hoggatt |
| 8,814,834 B2 | 8/2014 | Sund et al. |
| 8,870,827 B2 | 10/2014 | Young et al. |
| 8,945,053 B2 | 2/2015 | Vogt et al. |
| 9,364,610 B2 | 6/2016 | Kramer et al. |
| 9,364,611 B2 | 6/2016 | Kramer et al. |
| 2002/0042592 A1 | 4/2002 | Wilmot et al. |
| 2002/0046563 A1 | 4/2002 | Wakui et al. |
| 2002/0049406 A1 | 4/2002 | Hill et al. |
| 2002/0049407 A1 | 4/2002 | Hill et al. |
| 2005/0074498 A1 | 4/2005 | Tarara et al. |
| 2005/0148933 A1 | 7/2005 | Raven et al. |
| 2005/0177100 A1 | 8/2005 | Harper et al. |
| 2006/0079834 A1 | 4/2006 | Tennican et al. |
| 2007/0116729 A1 | 5/2007 | Palepu |
| 2007/0202163 A1 | 8/2007 | Rawas-Qalaji et al. |
| 2007/0293582 A1 | 12/2007 | Hill |
| 2008/0103490 A1 | 5/2008 | Edwards et al. |
| 2008/0281271 A1 | 11/2008 | Griffiths et al. |
| 2009/0171311 A1 | 7/2009 | Genosar et al. |
| 2010/0228190 A1 | 9/2010 | Griffiths et al. |
| 2010/0318035 A1 | 12/2010 | Edwards et al. |
| 2011/0092906 A1 | 4/2011 | Böttger et al. |
| 2011/0092917 A1 | 4/2011 | Wei et al. |
| 2011/0237681 A1 | 9/2011 | Batycky et al. |
| 2012/0016296 A1 | 1/2012 | Charles |
| 2012/0130318 A1 | 5/2012 | Young |
| 2012/0179137 A1 | 7/2012 | Rush et al. |
| 2012/0302989 A1 | 11/2012 | Kramer et al. |
| 2013/0018310 A1* | 1/2013 | Boyd .................... A61M 5/284 604/110 |
| 2013/0018313 A1 | 1/2013 | Kramer et al. |
| 2013/0023822 A1 | 1/2013 | Edwards et al. |
| 2013/0060232 A1 | 3/2013 | Adlon et al. |
| 2013/0178823 A1 | 7/2013 | Buchine et al. |
| 2013/0274707 A1 | 10/2013 | Wilmot et al. |
| 2013/0289791 A1 | 10/2013 | Kerrigan et al. |
| 2013/0317477 A1 | 11/2013 | Edwards et al. |
| 2013/0331788 A1 | 12/2013 | Kramer et al. |
| 2014/0088512 A1 | 3/2014 | Quinn |
| 2014/0276385 A1 | 9/2014 | Buchine et al. |
| 2014/0276430 A1 | 9/2014 | Baker et al. |
| 2014/0336589 A1 | 11/2014 | Sund et al. |
| 2015/0011975 A1 | 1/2015 | Anderson et al. |
| 2015/0174323 A1 | 6/2015 | Edwards et al. |
| 2015/0367073 A1 | 12/2015 | Standley et al. |
| 2015/0374925 A1 | 12/2015 | Standley et al. |
| 2016/0220764 A1 | 8/2016 | Durvasula et al. |

FOREIGN PATENT DOCUMENTS

| | | |
|---|---|---|
| WO | 9208506 A1 | 5/1992 |
| WO | 2005032523 A1 | 4/2005 |
| WO | 2008114035 A1 | 9/2008 |
| WO | 2008154092 A1 | 12/2008 |
| WO | 2009118754 A3 | 12/2009 |
| WO | 2010022870 A1 | 3/2010 |
| WO | 2010068415 A1 | 6/2010 |
| WO | 2011060541 A1 | 5/2011 |
| WO | 2011109340 A1 | 9/2011 |
| WO | 2012090168 A1 | 7/2012 |
| WO | 2012099898 A2 | 7/2012 |
| WO | 2013063707 A1 | 5/2013 |
| WO | 2014026694 A1 | 2/2014 |
| WO | 2014066731 A1 | 5/2014 |
| WO | 2014080020 A1 | 5/2014 |
| WO | 2014060563 A3 | 7/2014 |

(56) References Cited

FOREIGN PATENT DOCUMENTS

| | | |
|---|---|---|
| WO | 2014195183 A1 | 12/2014 |
| WO | 2014205463 A1 | 12/2014 |
| WO | 2015071289 A1 | 5/2015 |

* cited by examiner

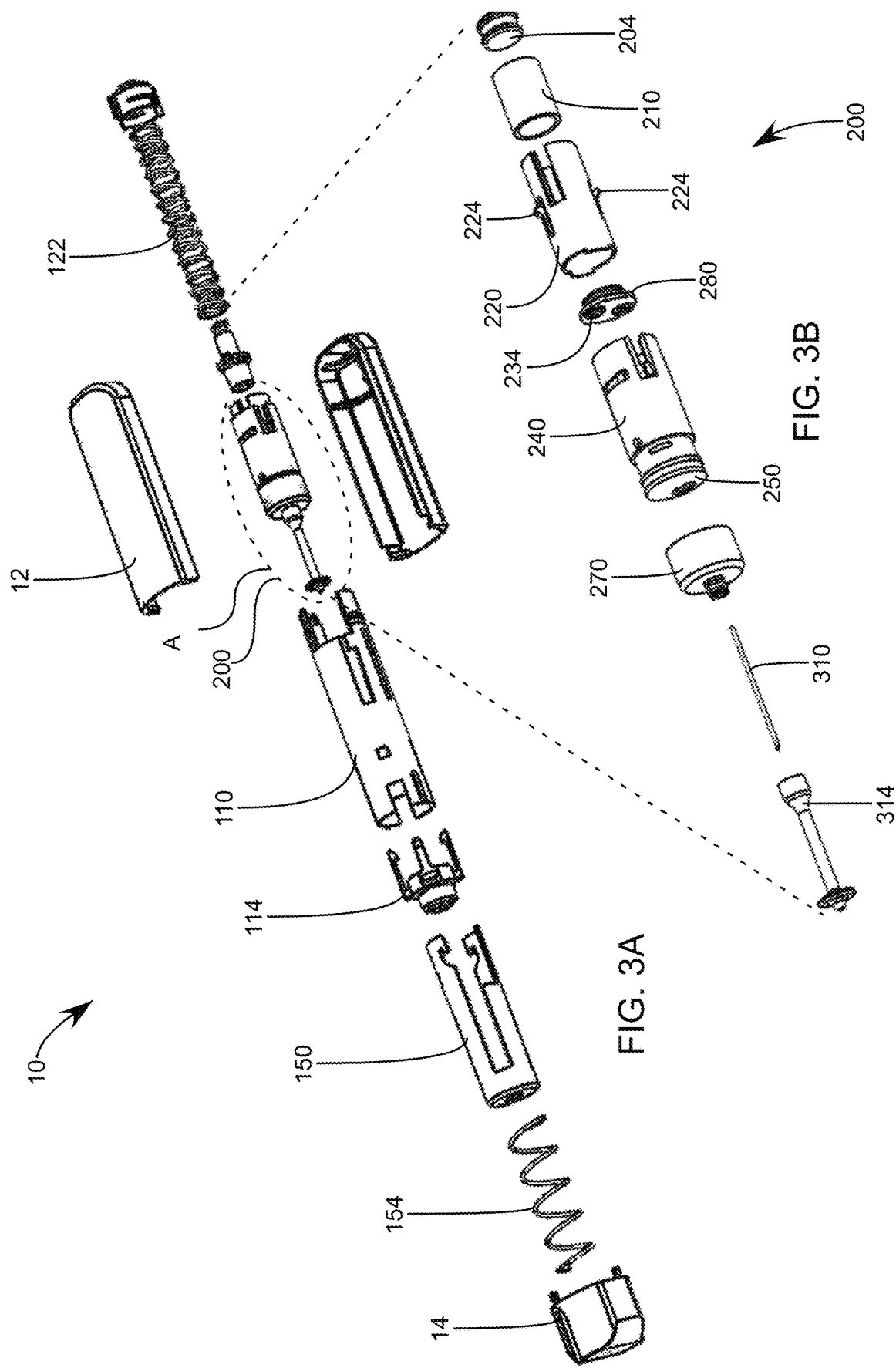

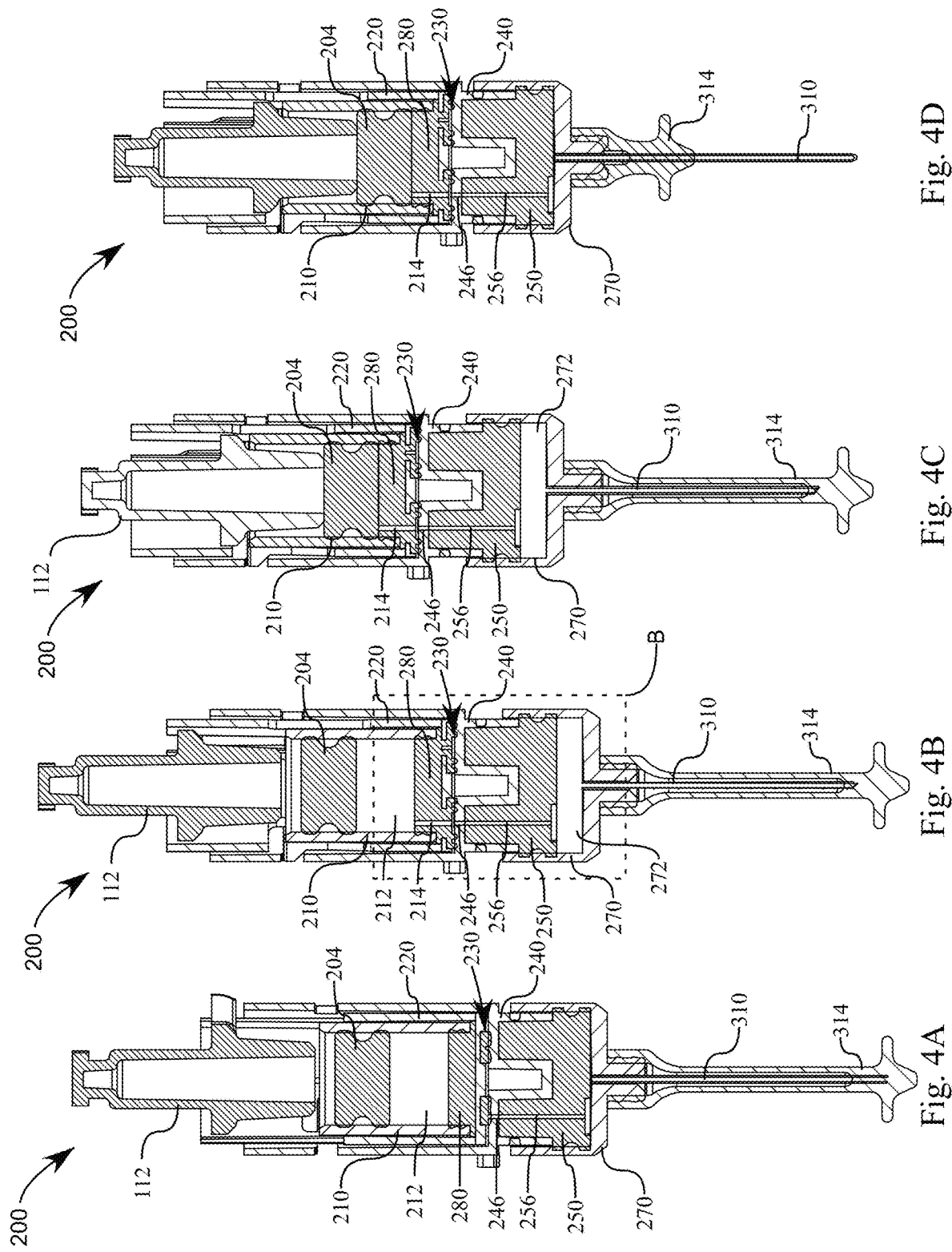

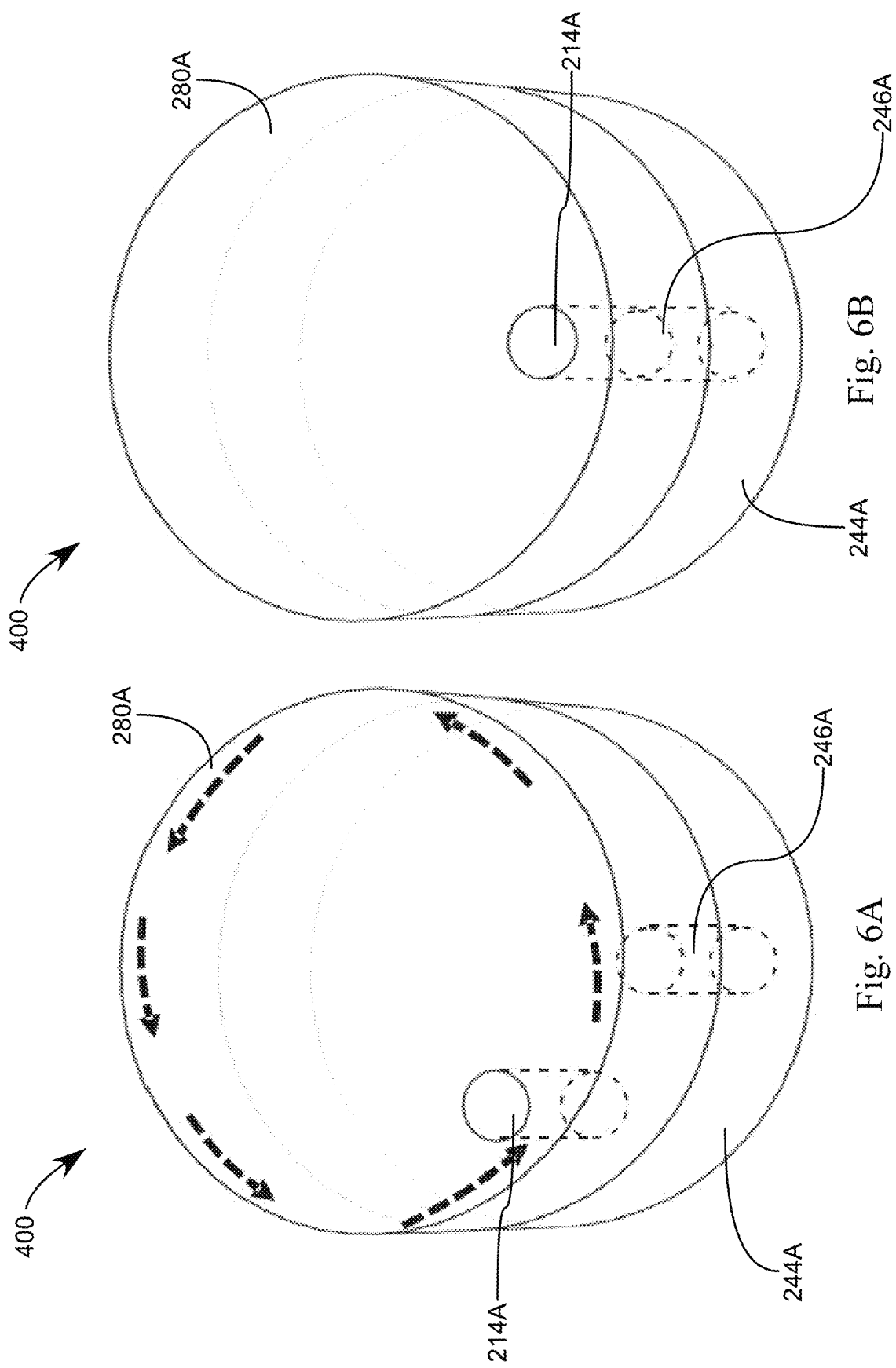

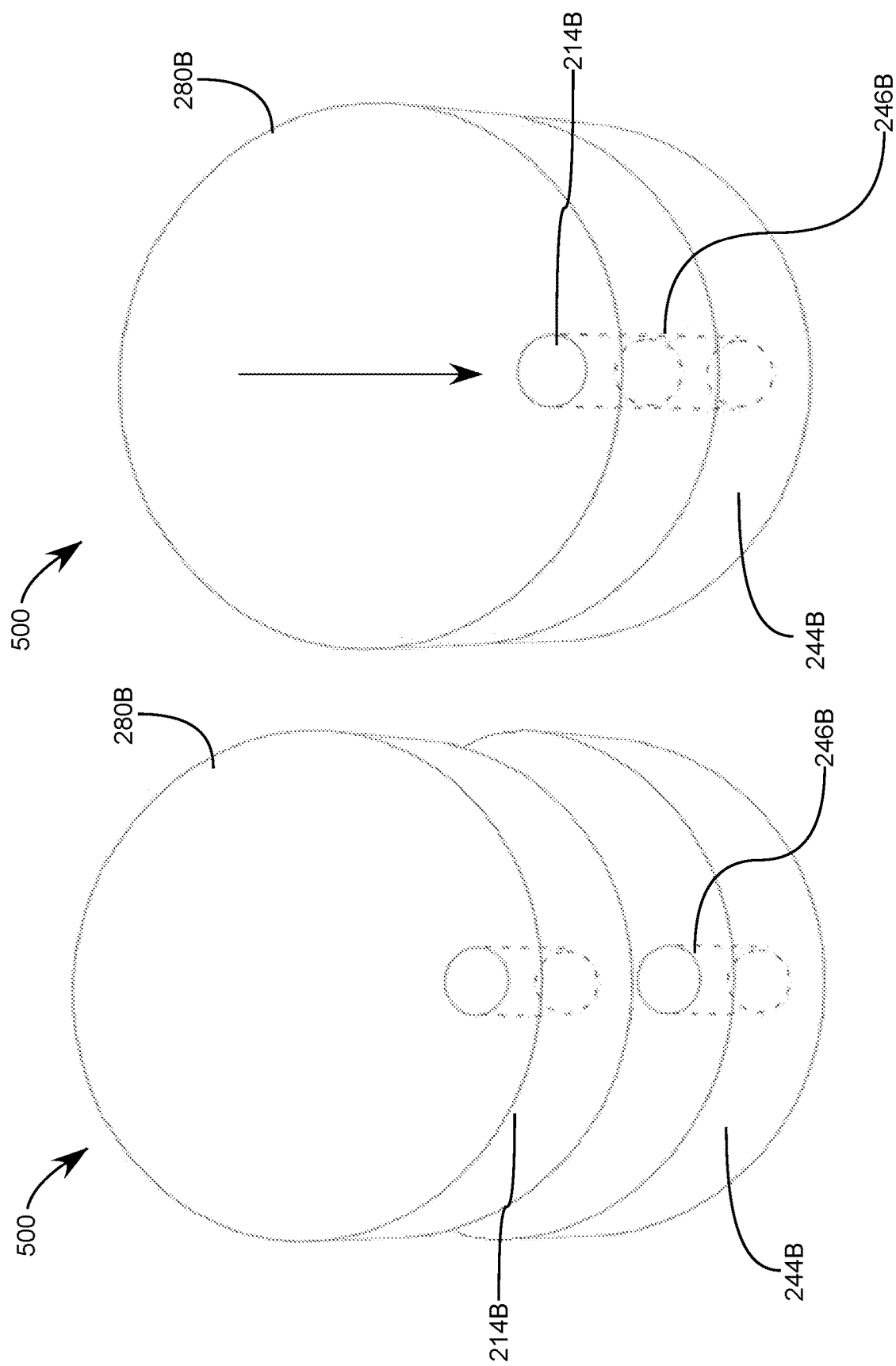

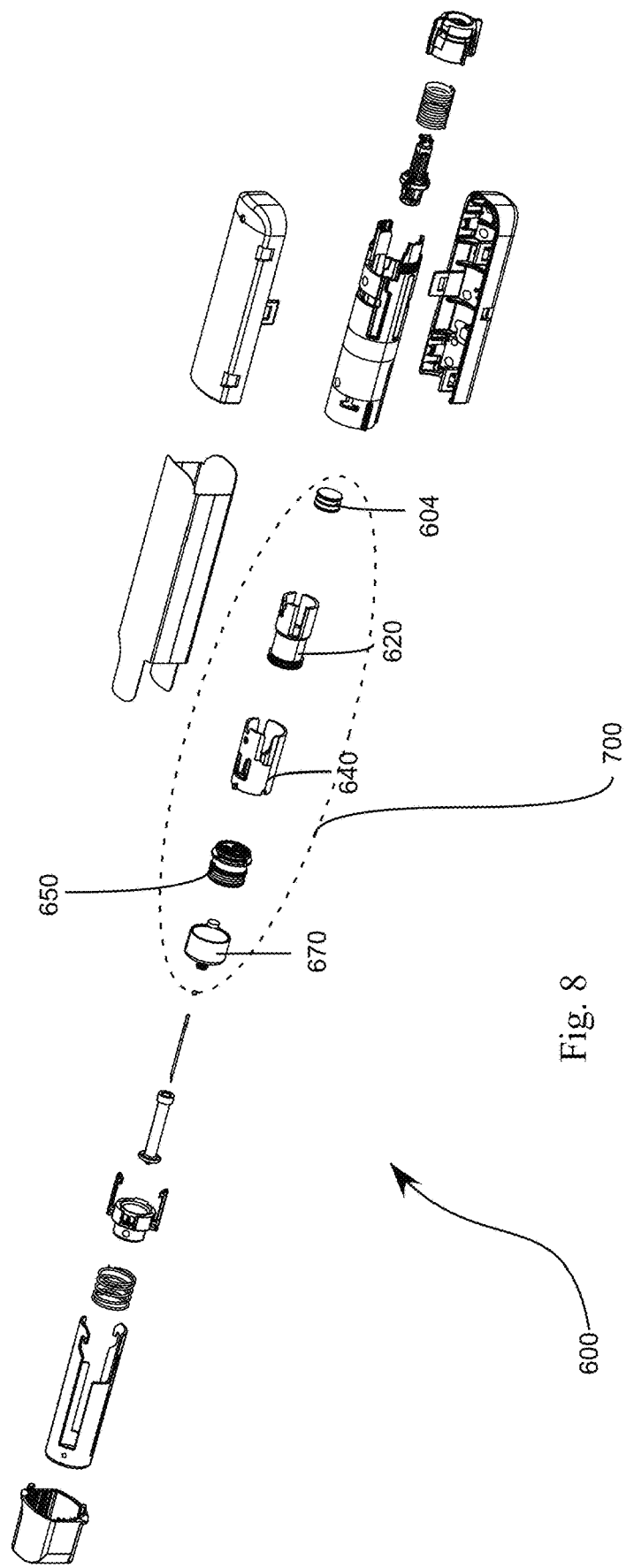

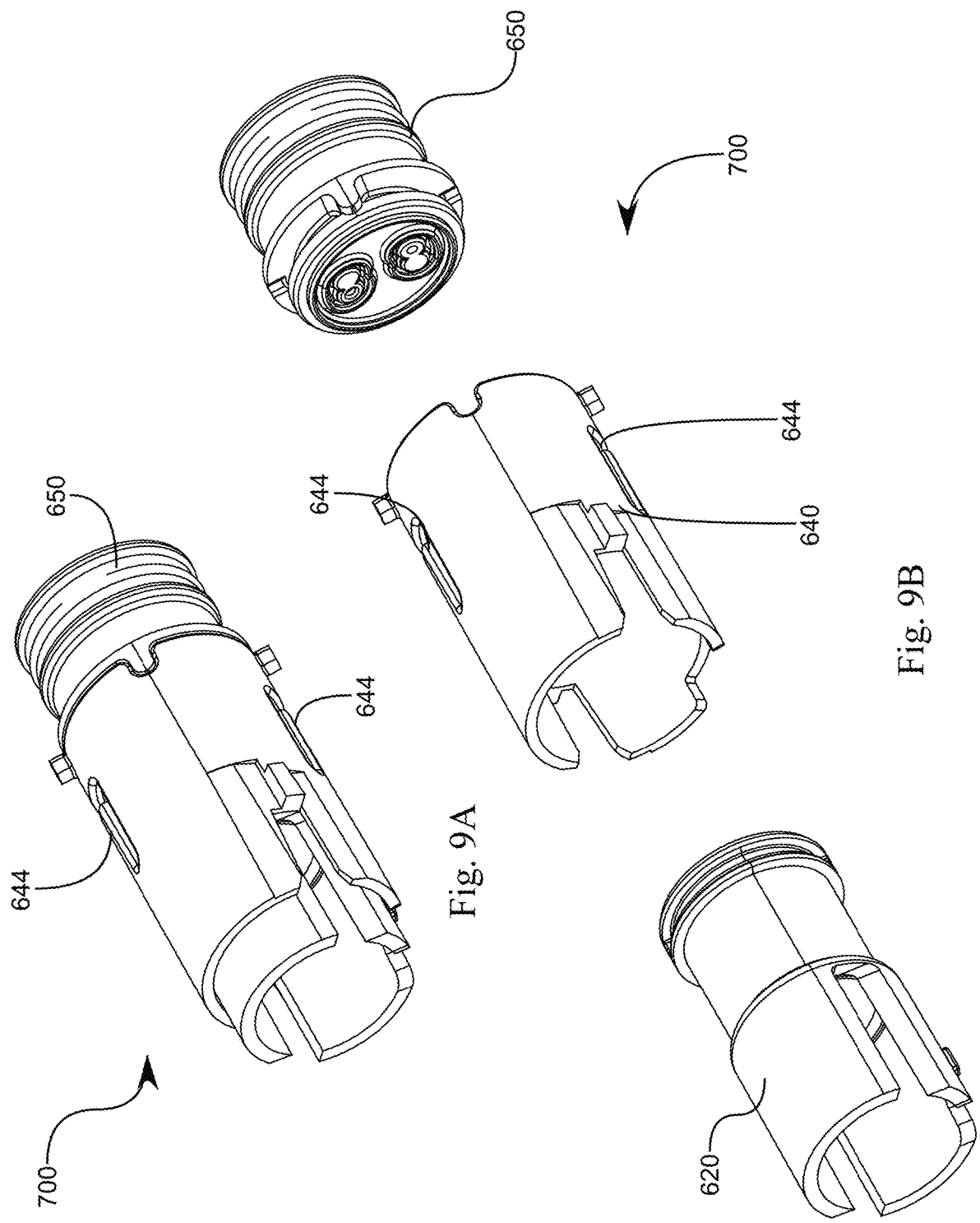

COMPRESSION SEAL FOR USE WITH A LIQUID COMPONENT STORAGE VIAL OF AN AUTO-INJECTOR

CROSS-REFERENCE TO RELATED APPLICATIONS

This application claims the benefit of U.S. Provisional. Patent Application Ser. No. 62/456,727 filed on Feb. 9, 2017; co-pending U.S. patent application Ser. No. 15/832, 346 which filed on Dec. 5, 2017; co-pending U.S. patent application Ser. No. 15/034,967; PCT Application number PCT/US15/45761 filed on Aug. 18, 2015, 2015; U.S. Provisional Patent Application No. 62/204,940 filed on Aug. 13, 2015; U.S. Provisional Patent Application No. 62/126,011 filed on Feb. 27, 2015; U.S. Provisional Patent Application No. 62/120,792 filed on Feb. 25, 2015; U.S. Provisional Patent Application No. 62/061,664 filed on Oct. 8, 2015; and U.S. Provisional Patent Application No. 62/038,386 filed on Aug. 18, 2014, which are all herein incorporated by reference in their entirety.

FIELD OF THE INVENTION

The present invention relates generally to auto-injectors and prefilled syringes and more particularly to auto injectors that store in a compact state but which allow for the preparation or mixing of various drug components prior to delivery to a patient.

BACKGROUND

It has been recognized that the shelf-life of the medications can be increased dramatically if the drug is stored as a dry medication separated from a diluent. In addition, these medications are often deployed in emergency situations where self-administration is preferred. However, the extra burden involved with dissolving a dry medication into the liquid dose just prior to injection typically requires multiple cumbersome steps by the user and often plagues the process with dosing errors, misfires, leakages, high injection failure rates, as well as other well-known issues. For this reason, it would be useful to have an easy to use autoinjector or pre-filled syringe device that automates the drug preparation process while also providing a platform requiring minimal user training and opportunity for user failure.

Currently available systems often include the use of a cartridge-based design with a fluid bypass. Actuation pushes fluid into cascading cartridges to mix fluid with additional fluids and/or dry medications. However, problems arise in these cascading cartridges wherein the bypasses can leak or have fluid escape in the wrong direction through the cascading plungers. This is often the result of the pressure in the system coupled with the need to have certain pressure relieving mechanisms. Plungers are generally not intended to be high pressure seals, as they are required to translate, thus limiting the amount of radial pressure the plunger can place on the wall in order to achieve the proper break-loose force. As such, the seal they provide is often inadequate over long periods of time and can cause sterility issues if not optimally designed. This leaking during storage causes premature fouling, while the leaking during injection decreases dose accuracy and precision. As such, a device having sealed chambers which are not under constant pressure may also provide increased seal durability and longevity.

The invention described herein provides a solution that seeks to solve the above identified problems, and thus, improves upon the durability, sterility, dose control, precision, accuracy, and freedom for orientation of the system when actuating.

SUMMARY

It has been recognized that various deficiencies of the prior art can be overcome by offering an auto-injection device having operable valves between separate and distinct chambers wherein a positive compression force provided between various valve components can increase the seal integrity and reduce leaking; and thus, preserve longevity and dosage accuracy.

In order to achieve the above described benefits contemplated herein is a medication mixing device which can include a housing wherein the housing contains a first chamber containing a first medicament component and a second chamber containing a second medicament component configured to be mixed with the first component.

The housing can also include a first displacement mechanism configured to selectively change an effective volume of the first chamber so as to drive the first medicament component into the second chamber for mixing.

A sealing structure can then be provided being configured to isolate the first chamber from the second chamber, wherein the sealing structure can include a first sealing component having a first sealing interface which can mate against or to a second sealing component having a second sealing interface that opposes the first sealing interface of the first sealing component. A first compression force can then be applied to or between the first and second sealing components so as to provide the sealing interfaces with a sealing force so as to form a seal.

It will then be understood that these opposing first and second sealing interfaces can be configured to mate or interface in such a manner so as to maintain at least one degree of freedom with respect to one another so as to allow relative motion and corresponding operation of the valve formed thereby in open or closed states.

In some embodiments the first sealing component can be provided with a first aperture which can operate as, or in fluidic communication with, an outlet of the first chamber, and wherein the second sealing component can be provided with a second aperture which provides fluidic communication with the second chamber wherein the first and second apertures can be selectively aligned. In some such embodiments the degree of freedom can be provided as a sliding translation which selectively aligns the first aperture with the second aperture. Alternatively, the degree of freedom can be provided as a radial translation which selectively aligns the first aperture with the second aperture. In yet additional such embodiments, the degree of freedom can be an axial rotation which selectively aligns the first aperture with the second aperture. In yet additional such embodiments, the degree of freedom can be a linear translation which selectively aligns the first aperture with the second aperture.

In yet additional embodiments, an inner vial can be utilized to form the first chamber wherein a vial sleeve can be provided which is configured to carry the inner vial. In some such embodiments an upper flange can be provided on the first sealing component between the inner vial and the vial sleeve, wherein a second compression force is provided between the vial sleeve and the inner vial so as to compress the upper flange between the inner vial and the vial sleeve thus sealing the first medicament component within the inner vial.

In some additional embodiments an intermediate support can be provided so as to house the vial sleeve, wherein the second sealing component is provided through the intermediate support, and wherein the first compressive force is provided between the vial sleeve and the intermediate support by providing one or more radially inward oriented protrusions which engage a top edge of the vial sleeve and bias the vial sleeve into the intermediate support thus creating the first compressive force.

It will then be appreciated that in some embodiments, rather than using a single displacement mechanism for both chambers, a second displacement mechanism can be provided which can be configured to selectively change an effective volume of the second chamber.

In yet additional arrangements the drug mixing device can be described as a device having an include a first chamber; a second chamber. A valve seal can then be provided which is disposed between the first chamber and the second chamber. This valve seal can include a first seal component disposed about an aperture provided in the first chamber; a second seal component in direct contact with the first seal component, the second seal component providing an inlet which provides selective fluid communication to the second chamber; wherein a compressive force can be provided by various structural components or a stored energy source which can then cause opposing surfaces of the first seal component and the second seal component to engage one another in sealing manner.

As previously discussed the formed seal can be configured to maintain at least one degree of freedom between the first and second seal components that enables the valve seal to change between a closed and open configuration through the various translations discussed previously.

A method of mixing a drug, utilizing the devices described above is also contemplated herein wherein in addition to providing the described device the method can also include various steps such as: providing a first medicament component into the first chamber; providing a second medicament component into the second chamber; moving a portion of the compression valve seal whereby the movement aligns a first and second aperture formed in the compression valve seal thereby forming a fluidic pathway between the first chamber and the second chamber; and displacing the first medicament component from the first chamber into the second chamber through the fluidic pathway, thereby causing first medicament component to mix with the second medicament component.

BRIEF DESCRIPTION OF THE FIGURES

FIG. 3A illustrates an exploded view of the medication mixing and delivery device of FIGS. 1A-C, which illustrates many of the individual parts for use therein;

FIG. 3B illustrates an exploded view of a mixing sub-assembly as outlined by selection A of FIG. 3A;

FIGS. 4A-D illustrate side cross-sectional views of the mixing sub-assembly and delivery assembly for use in the medication mixing and delivery device of FIGS. 1A-C;

FIGS. 6A-B illustrate perspective views of a rotary valve and operational principles thereof, the rotary valve being adaptable for use in any of the embodiments discussed herein;

FIGS. 7A-B illustrate perspective views of a radial valve, and operation principles thereof, the rotary valve being adaptable for use in any of the embodiments discussed herein;

FIG. 8 illustrates an exploded perspective view of an alternative embodiment of a medication mixing and delivery device having at least an alternative mixing assembly;

FIGS. 9A-B illustrate an enlarged perspective view, and an exploded perspective view of various components forming a portion of the alternative mixing assembly of the medication mixing and delivery device of FIG. 8;

DESCRIPTION

As discussed above, it has been recognized that various deficiencies of the prior art can be overcome by offering an auto-injection device having operable valves between separate and distinct chambers wherein a positive compression force provided between various valve components can increase the seal integrity and reduce leaking and thus preserve longevity and dosage accuracy. In order to achieve these and other benefits contemplated herein is a medication mixing device 10, components and embodiments of which are illustrated in FIGS. 1-7. The medication mixing device 10 can include a housing 12, wherein the housing 12 contains a first chamber and a second chamber containing components intended for mixing prior to delivery. It will be appreciated that the medication mixing device 10 can be actuated in a variety of states utilizing various means, however, for purposes of illustration FIGS. 1A-B illustrate a first actuation method which initiates a mixing step wherein a cap 14 is rotated with respect to the housing 12 so as to initiate mixing of the components contained within the various chambers within the housing. More detailed descriptions of methods of actuation are found at least in application numbers: Ser. Nos. 62/456,727; 15/832,346; 15/034,967; PCT/US15/45761; 62/204,940; 62/126,011; 62/120,792; 62/061,664; 62/038,386 to which priority is claimed above, and which are all incorporated by reference herein.

Figure 2A:
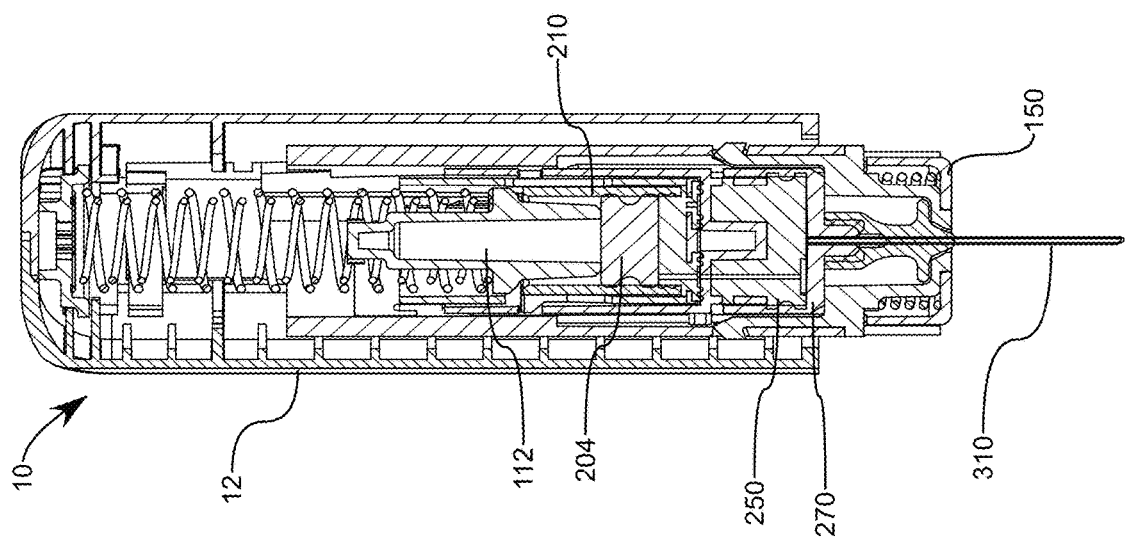
FIGS. 2A-B illustrate side cross-sectional views of the medication mixing and delivery device of FIGS. 1A-C through various stages of a second actuation or delivery step.
Figure 2B:
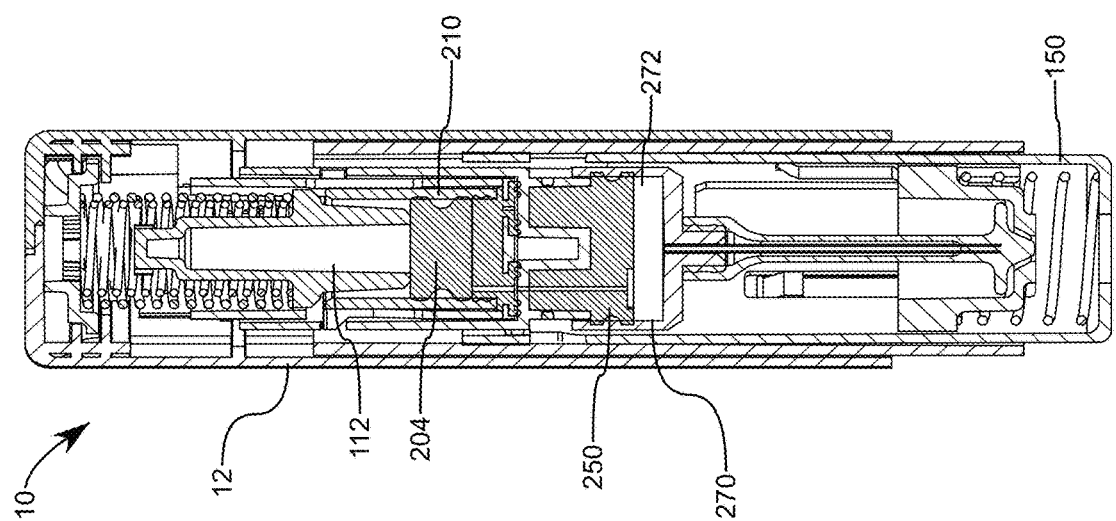
Figure 5:
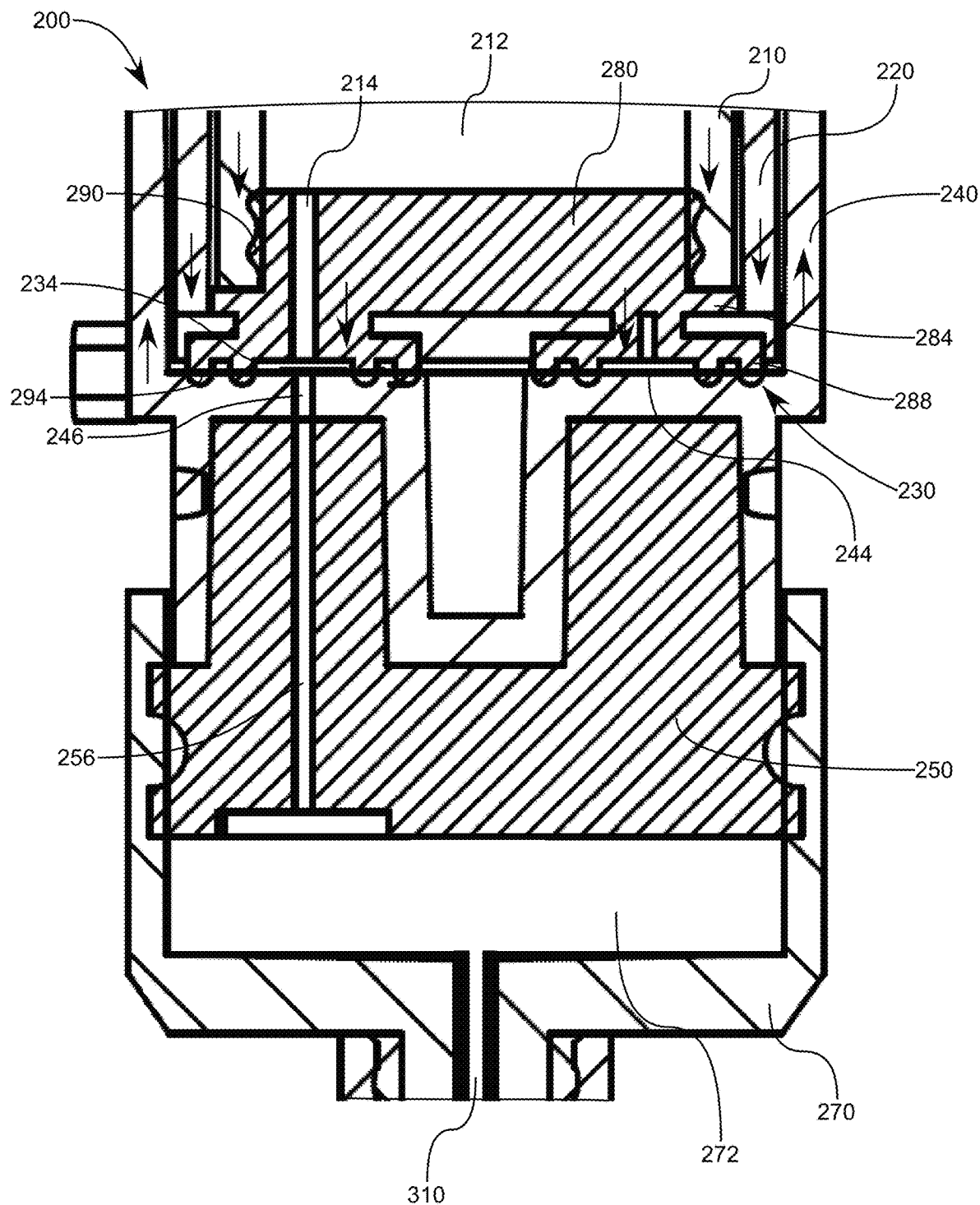
FIG. 5 illustrates an enlarged cross-sectional view of the area as outlined by selection B indicated in FIG. 4B.
Figure 10A:
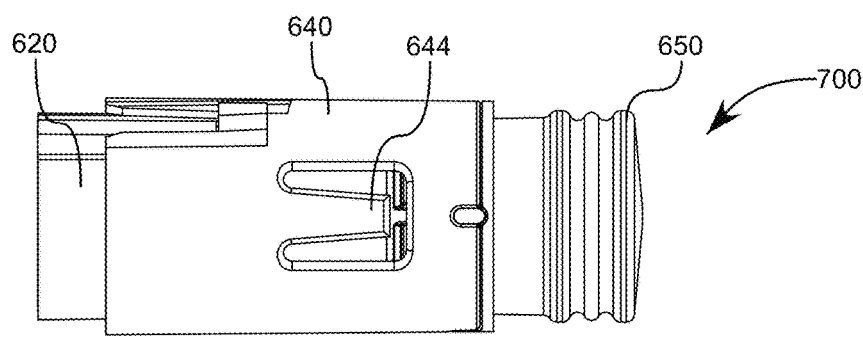
FIGS. 10A-B illustrate side and horizontal cross-sectional views of various components forming a portion of the alternative mixing assembly of the medication mixing and delivery device of FIGS. 8.
Figure 10B:
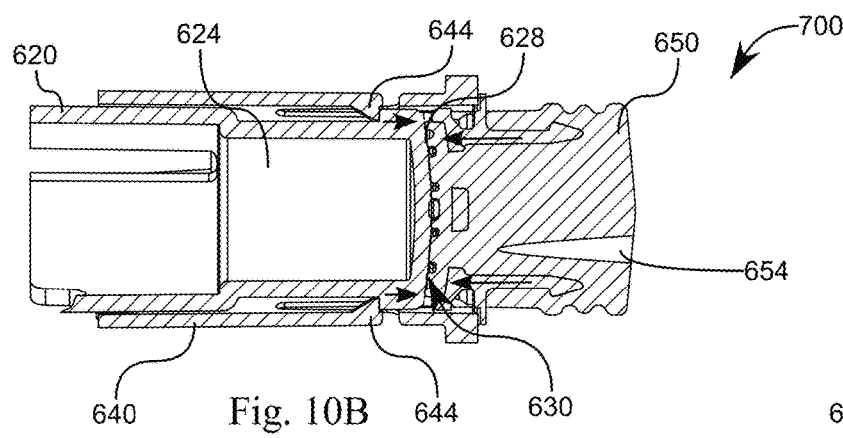
Figure 11A:
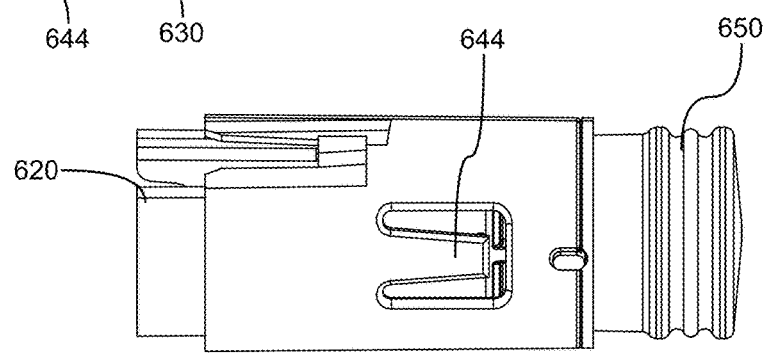
FIGS. 11A-B illustrate side and horizontal cross-sectional views of various components forming a portion of the alternative mixing assembly of the medication mixing and delivery device of FIG. 8 in a slightly axially rotated configuration.
Figure 11B:
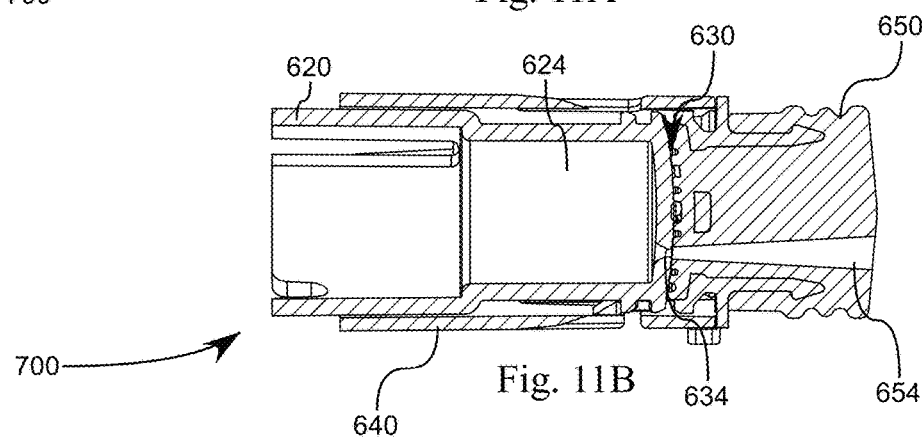

FIGS. 2A-B illustrate side cross-sectional views of the medication mixing device 10 through a second delivery step while FIGS. 4A-D illustrate various stages of unmixed, open prior to mixing, mixed, and ejected states. These views better illustrate the first chamber 212 as contained within inner vial 210, wherein a first medicament component can be contained therein, preferably as a liquid diluent or injectable medicament suspension component.

These views also illustrate a second chamber 272, as contained in a second vial 270, which is configured to contain a second medicament component configured to be mixed with the first medicament component. It will also be appreciated that the second medicament component can be provided as a dry component. Further, this second medicament component can also be provided within a channel provided between the first and second chambers so as to ensure mixing as the first medicament component passes from the first chamber into the second chamber.

The medication mixing device 10 can also include a first displacement mechanism 204, which can be provided as a plunger, wherein the first displacement mechanism 204 can be configured to selectively change an effective volume of the first chamber 212 so as to drive the first medicament component into the second chamber for mixing.

A sealing structure 230 can then be provided being configured to isolate the first chamber 212 from the second chamber 272, wherein the sealing structure 230 can include a first sealing component 280 having a first sealing interface 234 which can mate against, or to, a second sealing component, herein illustrated as an intermediate support 240, wherein the intermediate support includes a second sealing interface 244 provided as an interior bottom surface thereof. In this manner the second sealing interface 244 opposes the first sealing interface 234 of the first sealing component 280. A first compression force can then be applied to or between the first and second sealing components so as to provide the sealing interfaces with a sealing force so as to form a seal.

It will then be understood that these opposing first and second sealing interfaces can be configured to mate or interface in such a manner so as to maintain at least one degree of freedom with respect to one another so as to allow relative motion and corresponding operation of the valve formed thereby in open or closed states. This degree of freedom can be described as a plane which exists between the first sealing component and the second sealing component wherein the first sealing component and the second sealing component can slide, either rotationally or radially, with respect to one another.

In some embodiments the first sealing component 280 can be provided with a first aperture 214 which can operate as, or in fluidic communication with, an outlet of the first chamber 212, and wherein the second sealing component 240 can be provided with a second aperture 246 which provides fluidic communication with the second chamber 272 wherein the first and second apertures can be selectively aligned through the relative motion between the first sealing component and the second sealing component.

In some such embodiments the degree of freedom can be provided as a sliding translation which selectively aligns the first aperture with the second aperture. Wherein in some such embodiments the sliding or translation can be provided as a radial translation as illustrated in FIGS. 7A-B which selectively aligns the first aperture with the second aperture. In yet additional such embodiments the degree of freedom can be provided as an axial rotation which selectively aligns the first aperture with the second aperture as illustrated in FIGS. 6A-B.

In the exemplary embodiments illustrated herein, an inner vial 210 can be utilized to form the first chamber 212 wherein a vial sleeve 220 can be provided which is configured to carry the inner vial 210. In some such embodiments an upper flange 284 can be provided on the first sealing component 280 between the inner vial 210 and the vial sleeve 220, wherein a second compression force is provided between the vial sleeve 220 and the inner vial 210 so as to compress the upper flange 284 between the inner vial 210 and the vial sleeve 220 thus sealing the first medicament component within the inner vial wherein the only exit path is through the aperture 214 when properly aligned. In some such embodiments the vial sleeve 220 can be provided with one or more radially inwardly biased or oriented protrusions 224 which can be configured to engage a top edge of the inner vial 210 and bias the vial downward into the interior of the vial sleeve 220 and thus creating the first compressive force which sandwiches the upper flange 284 between the vial sleeve 220 and a bottom edge the vial 220.

Additionally the first seal component can be provided with a lower flange 288 which can be provided between the vial sleeve 220 and an interior edge of the intermediate support 240 wherein a compressive force provided between the vial sleeve 220 and the interior of the intermediate support can then cause the lower flange 288 to be sandwiched or pressed between the lower edge of the vial sleeve 220 and the interior surface of the intermediate support which then provides a double seal and prevents fluid, when compressed within the inner vial 210 from passing into the interior of the housing 12 between the via sleeve 220 and the housing 12, or between the vial sleeve 220 and the intermediate support 240.

In some embodiments the seal component can also be provided with contours or protrusions 290 and 294 respectively which can be placed strategically to allow for deformation about respective surfaces and increase the sealing reliability and equalize sealing force distribution, particularly through translation against opposing surfaces such as the inner vial wall, or against the second sealing interface surface 244.

It will then be appreciated that in some embodiments, rather than using a single displacement mechanism for both chambers, a second displacement mechanism 250 can be provided which can be configured to selectively change an effective volume of the second chamber. In the embodiments shown the second displacement mechanism 250 is provided as a plunger about a lower exterior surface of the intermediate support 240, wherein the second displacement mechanism 250 extends into and mates with an interior circumferential surface of the second chamber 272. The intermediate body 240 and plunger 250 can be provided with apertures 246 and 256 provided respectively therethrough which, when aligned to the outlet aperture 214 of the first chamber 212, together act as a fluidic pathway into the second chamber 272 and allow the fluid to pass through them and mix with the second medicament component which can be contained within this pathway, or within the second chamber itself. In this manner, the movement of the first medicament component into the second chamber provides the necessary mixing of the first and second medicament components.

In this manner the drug mixing device 10 can be described as a device having an include a first chamber; a second chamber. A valve, as provided by the selective misalignment or alignment of aperture 214 and aperture 246.

A method of mixing a drug, utilizing the devices described above is also contemplated herein wherein in addition to providing the described device the method can also include various steps such as: providing a first medicament component into the first chamber; providing a second medicament component into the second chamber; moving a portion of the compression valve seal whereby the movement aligns a first and second aperture formed in the compression valve seal thereby forming a fluidic pathway between the first chamber and the second chamber; and displacing the first medicament component from the first chamber into the second chamber through the fluidic pathway, thereby causing first medicament component to mix with the second medicament component.

FIGS. 3A-B illustrate an exploded view of an auto-injector 10 in accordance with at least one embodiment of the present invention. This exploded view illustrates the various internal components within the housing 12 and the cap 14. The auto-injector 10 can be provided which includes a mixing assembly 200. The drug mixing system is provided with at least one chamber that stores at least one medicament components, such as a wet solvent, diluent, or suspension fluid. The drug mixing assembly 200 can further be provided with a second vial or container 270 about an end thereof which can hold at least one second medicament component, such as a dry drug ingredient, wherein the second vial is configured to receive the first medicament component. As shown herein, the first and second chambers can be separate and distinct chambers with distinct and separable structure forming their respective volumes, and can be movable with respect to one another.

As shown herein the first and second chambers can be configured to translate toward and away from one another, slide radially with respect to one another, as well as rotate with respect to one another along a common axis or any combination thereof.

The housing can include a pre-loaded energy source 122 which is shown here as a spring, or which can be embodied as a compressed air chamber, which is not shown but could be adapted by those having skill in the art. The spring can be configured to provide a driving force and counter force between an inner plunger shaft 112, and transferred to various components of a mixing assembly 200 through various stages, as will be discussed below. The mixing assembly 200 can be contained within a frame 110, wherein individual components of the mixing assembly 200 can be configured to selectively rotate within the housing 12. The spring can also be configured to provide one or more of the compressive forces to provide the sealing on the upper and lower flanges 284 and 288 respectively, as discussed above by transferring a force through the plunger shaft 112 and into an upper edge or rim of either the inner vial 210 or the vial sleeve 220.

The mixing assembly 200 can be retained within the frame using a frame cap 114 which can be formed separately or unitarily with the frame 110. The frame cap 114 prevents the mixing assembly 200 from pushing through the frame 110 and exiting the housing 12 completely upon delivery or injection and provides a counter force to the extension of the spring 122 so as to drive the mixed first and second medicament components from the second chamber 272.

The frame cap 114 can also help retain a needle guard 314 when the injection needle punctures or pierces through the needle guard and, which can be provided to better preserve sterility of a needle 310, when in a state to be inserted into a user. As such, when driven downward the mixing assembly 200 bottoms out and is retained by the frame cap 114 while the needle 310 can then penetrate the needle guard 314 and extend beyond the housing so as to deliver the mixed medicament components to an injection site.

Also shown herein is a needle shield 150 and a needle shield spring 154 which can be provided between the frame 110 and the housing 12 at an injection end of the housing 12. The needle shield 150 can operate as a trigger for a second delivery step, as illustrated in FIGS. 2A-B, and the needle shield spring 154 can be configured to bias the needle shield 150 axially downward so as to continuously restrict inappropriate exposure of the needle 310 prior to and after injection. These functions are described in more detail in the related applications.

Figure 1C:
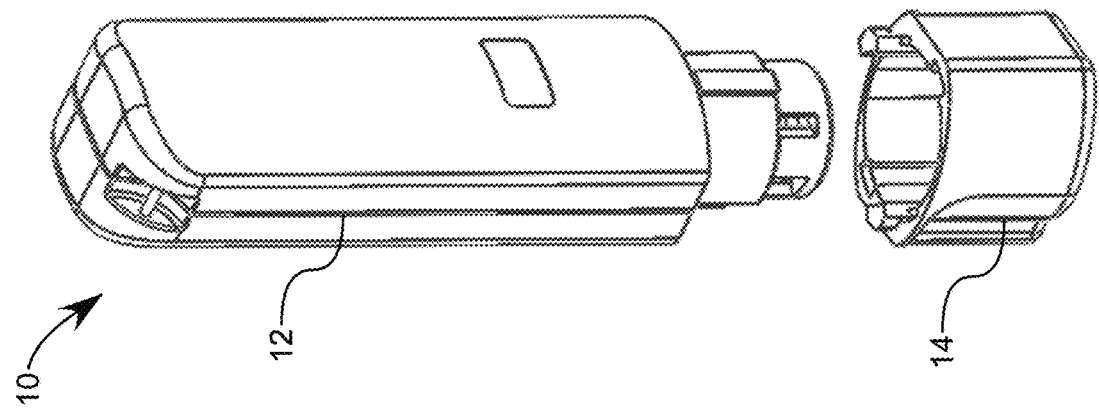
FIGS. 1A-C illustrate perspective exterior views of a medication mixing and delivery device illustrative of various aspects of the present invention through various stages of a first actuation step.
Figure 1B:
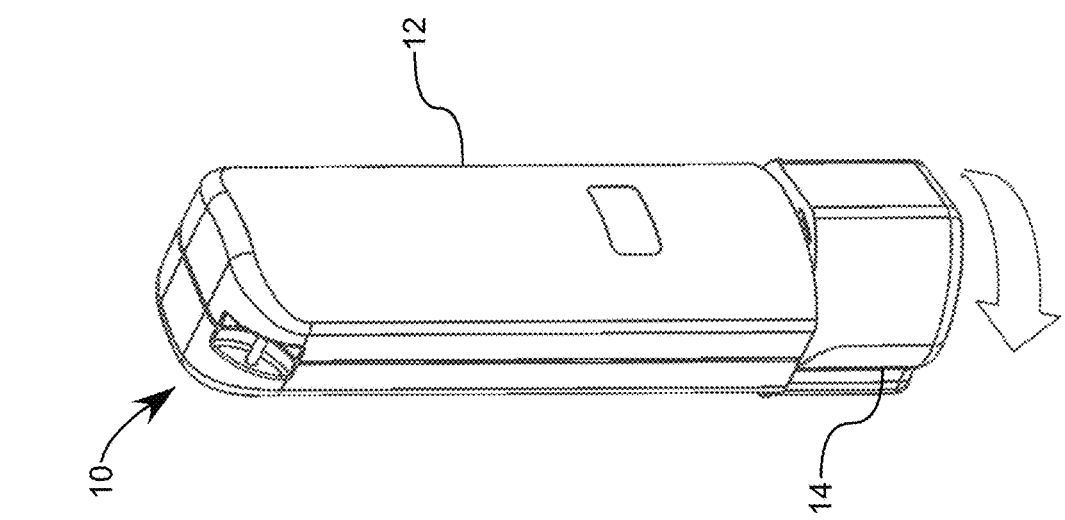
Figure 1A:
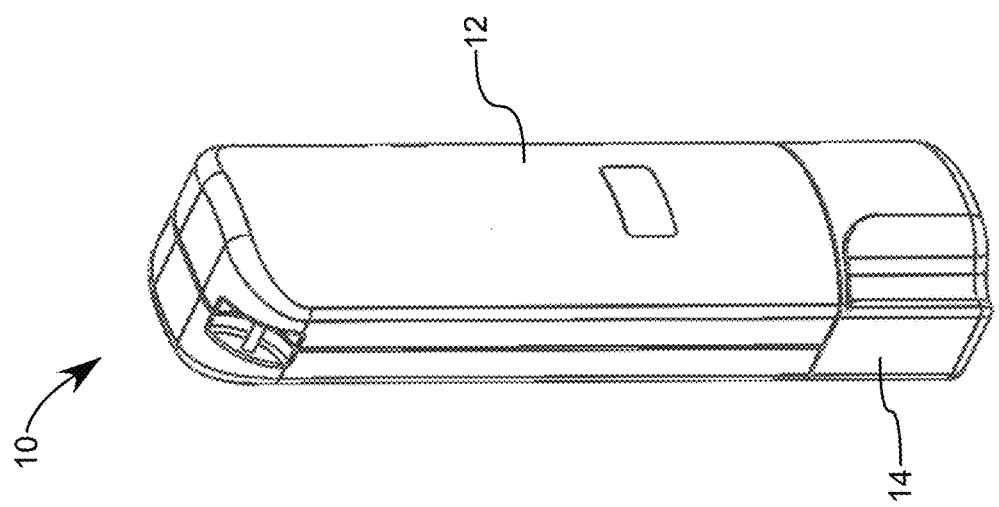

The frame 110 and portions of the mixing assembly 200 can be configured to rotate together within the housing when an axially torsional force is applied between the cap 14 and the housing 12, as illustrated in FIGS. 1A-C. The cap 14 can thus be coupled in a radially fixed manner to the frame 110 which is in turn coupled to certain components of the mixing assembly 200, and a driver interface 118 can also be provided which is rigidly coupled to the housing 12 as well as coupled in a radially fixed manner to alternative portions of the mixing assembly 200 such as to the inner plunger shaft 112. In this manner the axially torsional force and counter force applied between the cap and the housing can be transferred into and caused to actuate certain components of the mixing assembly 200.

The mixing assembly can include an inner plunger shaft 112 and an inner plunger 204 which together operate as the first displacement mechanism discussed above. The first displacement mechanism can be configured to reduce the effective volume of the first chamber, which will initially contain the first medicament component, i.e. a liquid component of the medicament.

The plunger is configured to interface with an inner vial 210 which forms the first chamber. The inner vial can be housed within a vial sleeve 220, or alternatively the vial sleeve 220 and the inner vial 210 can be formed unitarily of a single material.

The vial sleeve 220 can then interface with a rotational valve seal 280 which sits within an intermediate support 240. The intermediate support 240 can have a second displacement mechanism 250, i.e. a second plunger, which is coupled thereto, the second plunger being configured to reduce the effective volume of a second chamber located within a second vial 270.

The second vial 270 can then be provided with a delivery assembly 300 affixed thereto which can include a needle 310 or cannula as well as a needle guard 314 or other barrier configured to maintain sterility of the delivery assembly prior to use.

The vial sleeve can be provided with one or more radially inwardly extending protrusions which correspond with a top edge of the glass vial. By inserting the glass vial and providing a downward or compressive force, wherein the radially inwardly extending protrusions of the vial sleeve will engage the upper edge of the vial itself and maintain the compressive force. The compressive force between the vial itself and the vial sleeve can be configured to sandwich an upper flange of the compression seal and thus prevent escape of the fluid contained in the wet chamber into the area between the vial and the vial sleeve. In some embodiments the compression seal can further include an additional upward extension which extends into the interior cavity of the vial and acts as a stopper for the plunger upon injection. This upward extension can also be provided with one or more extensions which can be configured to interact or engage with corresponding grooves formed onto an interior surface of the vial itself, thus adding another series of seals so as to prevent leaking and premature fouling of the drugs contained therein.

It will be appreciated that the various apertures and/or the fluidic passageway can be misaligned through various means, such as provided in a sidewall, and axially displaced, or placed in a bottom end wall and either axially twisted or radially translated.

FIGS. 6A-B illustrate the principles of operation of a rotary valve seal 400 for use in the embodiments discussed above. A rotary valve can be formed wherein a fluidic pathway is established by rotating one aperture with respect to the other. In this exemplary illustration the aperture 214A formed in component 280A can be provided in a bottom portion of a vial which forms a chamber, and the secondary aperture 246A formed in component 244A provided through a bottom interfacing portion of the seal 400, which can be the inlet to the remaining portion of a fluidic channel leading to another chamber. FIG. 6A illustrates a closed configuration wherein the two apertures are misaligned and fluid communication does not exist. FIG. 6B illustrates an open configuration wherein the two apertures are aligned and fluid communication is established. It will be appreciated that in order to form a better seal, one or both of the components (244A, 280A) can be formed of a material having deformable properties such as rubber or silicone. In another embodiment, one of the components is rubber and another is hard plastic. In another embodiment each of the sealing surfaces are made up of a combination of hard plastic and elastomeric materials in one interface.

FIGS. 7A-B illustrate the principles of operation of a radial valve seal 500 for use in the embodiments discussed above. A rotary valve can be formed wherein a fluidic pathway is established by radially sliding one aperture with respect to the other. In this exemplary illustration the aperture 214B formed in component 280B can be provided in a bottom portion of a vial which forms a chamber, and the secondary aperture 246B formed in 244B provided through a bottom interfacing portion of the seal 500, which can be the inlet to the remaining portion of a fluidic channel leading to another chamber. FIG. 7A illustrates a closed configuration wherein the two apertures are misaligned and fluid communication does not exist. FIG. 7B illustrates an open configuration wherein the two apertures are aligned and fluid communication is established. It will be appreciated that in order to form a better seal, one or both of the components (244B, 280B) can be formed of a material having deformable properties such as rubber or silicone. In another embodiment, one of the components is rubber and another is hard plastic. In another embodiment each of the sealing surfaces are made up of a combination of hard plastic and elastomeric materials in one interface.

FIGS. 8-11 illustrate an alternative embodiment of a drug mixing and delivery device 600 which includes various alternative arrangements, namely in the mixing assembly 700, which can eliminate the need for at least one sealing compressive force. In particular the mixing assembly 700 can include a vial sleeve 620 with a vial portion 624 which is integrally formed into the interior of the sleeve 620 thus eliminating the need to have a separate and distinct vial as shown in the previous embodiments. it will be appreciated that this alternative embodiment still includes two separate and distinct chambers formed by the vial 670 and the vial sleeve 620 respectively, wherein associated separate and distinct displacement mechanisms 604 and 650 are configured to reduce the effective volume of their respective chambers.

Similar to the embodiment above, this medication mixing and delivery device includes a valve assembly 630 which operates between closed and open positions so as to retain a first medicament component in the vial portion 624 for mixing with a second medicament component located outside the vial portion, i.e. in the second vial 670. Similarly, an outlet 634 can be placed in selective alignment with an inlet or fluid passageway 654 leading to the second chamber, shown herein as passing through the second displacement mechanism 650.

The valve assembly is formed primarily from a bottom edge surface 628 of the vial sleeve 620 which abuts against an opposing surface of the second displacement mechanism 650 or an interior surface of the corresponding intermediate support 640. The intermediate support 640 can provide structural support and function to various components, including at least carrying the second displacement mechanism, various actuation features such as tabs or protrusions which can be acted upon so as to open or close the valve assembly, as well as offer structural support to the vial sleeve so as to provide a compressive sealing force between itself and the vial sleeve or between the vial sleeve 620 and the upper edge of the second displacement mechanism 250, as illustrated here.

The compressive force discussed above can be applied by providing tabs or springs 644 which can be biased inward such that when the vial sleeve is inserted into the intermediate support to a certain compressive depth, the tabs 644 can flex into the central portion and engage a corresponding lip provided on the exterior surface of the vial sleeve thus retaining the vial sleeve in a compressive arrangement against the back or opposing surface of the second displacement mechanism 650, or alternatively to an interior surface of the intermediate support, if provided, but not shown here.

As shown herein, the displacement mechanism 650 can be retained in an axially fixed position with respect to the intermediate support 640 through corresponding protrusions, lips, and/or grooves. In this manner it can oppose and seal in response to a compressive force through the vial sleeve 620. This compressive force, particularly when the outlet 634 is misaligned from the channel 654 then results in a positive sealing force between the vial sleeve 620 and the opposing surface of the displacement mechanism.

In some embodiments the vial sleeve 620 can be formed of a thermoplastic overmolded over a glass vial portion. Alternatively, the entire vial sleeve can be formed of a unitary structure having uniform material forming the structure thereof. Similarly, the second displacement mechanism 650 can be rubberized material overmolded over and into the intermediate support 640.

Similar overmolding can be utilized in any of the structures of any of the embodiments disclosed herein.

It will be understood that the plungers or valve components discussed in any of the embodiments herein can be formed of an appropriate sealing substance such as rubber, silicone, or virtually any malleable substance which can be individually tailored to be compatible with the substances of the first or second medicament components.

We claim:
1. A medication mixing device comprising:
   a housing;
   a first chamber having an outlet and provided within the housing, the first chamber containing a first medicament component;
   a second chamber having an inlet and provided within the housing;
   a second medicament component provided within the housing and outside the first chamber;
   a sealing structure isolating the first chamber from the second chamber, the sealing structure further comprising:
      a first sealing component having a first sealing interface, a second sealing component having a second sealing interface that opposes the first sealing interface of the first sealing component, wherein a compression force being applied to the first and second sealing components causes the first and second sealing interfaces to form a seal; and at least one tab interfacing with the first chamber and configured to maintain the compression force between the first sealing component and the second sealing component.

2. The medication mixing device of claim 1, wherein the compression force allows the first sealing component and the second sealing component to maintain at least one degree of freedom that is an axial rotation which selectively aligns the outlet of the first chamber with the inlet of the second chamber.

3. The medication mixing device of claim 1, wherein the at least one tab interfaces with a corresponding lip about a sidewall of the first chamber to create the compression force.

4. The medication mixing device of claim 3, wherein a portion of the second sealing component is affixed to a portion of an intermediate support, and wherein the intermediate support structurally supports the at least one tab, thereby upon inserting the first chamber into the intermediate support causes the first chamber to press the first sealing component against the second sealing component, which compression force is maintained by the at least one tab engaging the corresponding lip on the sidewall of the first chamber.

5. The medication mixing device of claim 1, wherein the first chamber is comprised of:

an inner vial forming an interior volume of the first chamber; and a vial sleeve carrying the inner vial.

6. The medication mixing device of claim 5, wherein the inner vial and the vial sleeve are unitarily formed.

7. The medication mixing device of claim 1, wherein the first sealing component is provided with a first aperture in fluidic communication with the outlet of the first chamber, and wherein the second sealing component is provided with a second aperture which provides fluidic communication with the inlet of the second chamber.

8. The medication mixing device of claim 7, wherein the compression force allows the first sealing component and the second sealing component to maintain at least one degree of freedom that is a sliding translation which selectively aligns the first aperture with the second aperture.

9. The medication mixing device of claim 7, wherein the compression force allows the first sealing component and the second sealing component to maintain at least one degree of freedom that is a linear translation which selectively aligns the first aperture with the second aperture.

10. A medication mixing device, the device comprising:

a housing;

a first chamber, disposed within the housing;

a second chamber, disposed within the housing;

a valve seal disposed between the first chamber and the second chamber, the valve seal further comprising:

a first seal component disposed about an aperture provided in the first chamber;

a second seal component in direct contact with the first seal component, the second seal component providing an inlet which provides selective fluid communication to the second chamber; and a pair of tabs interfacing with the first chamber and configured to provide a compression force about the first sealing component and the second sealing component, thus forming a seal, wherein the formed seal maintains at least one degree of freedom between the first and second seal components that enables the valve seal to change between a closed and open configuration.

11. The medication mixing device of claim 10, wherein the degree of freedom is an axial rotation, wherein the axial rotation selectively aligns an aperture provided in the first seal component with the inlet of the second seal component.

12. The medication mixing device of claim 10, wherein the degree of freedom is a planar translation, wherein the planar translation selectively aligns an aperture provided in the first seal component with the inlet of the second seal component.

13. The medication mixing device of claim 10, further comprising an intermediate support having a first portion affixed to the second sealing component and a second portion connected to the pair of tabs.

14. The medication mixing device of claim 10, wherein a sidewall of the first chamber has a lip configured to interface with the pair of tabs.

* * * * *